United States Patent
Spataro et al.

(10) Patent No.: US 12,263,316 B2
(45) Date of Patent: Apr. 1, 2025

(54) FLUID PATH OPTIMIZATION IN CATHETER INSERTION SYSTEMS

(71) Applicant: Bard Access Systems, Inc., Salt Lake City, UT (US)

(72) Inventors: Joe Spataro, Cottonwood Heights, UT (US); Austin J. Mckinnon, Herriman, UT (US); Bryan Haymond, Emigration Canyon, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 259 days.

(21) Appl. No.: 17/557,924

(22) Filed: Dec. 21, 2021

(65) Prior Publication Data

US 2022/0193378 A1    Jun. 23, 2022

Related U.S. Application Data

(60) Provisional application No. 63/128,677, filed on Dec. 21, 2020.

(51) Int. Cl.
*A61M 25/06* (2006.01)
*A61M 25/01* (2006.01)

(52) U.S. Cl.
CPC . *A61M 25/0693* (2013.01); *A61M 2025/0183* (2013.01)

(58) Field of Classification Search
CPC .............. A61M 25/0693; A61M 5/281; A61M 2025/0183; A61M 25/0606;
(Continued)

(56) References Cited

U.S. PATENT DOCUMENTS

| 1,013,691 A | 1/1912 | Shields |
| 3,225,762 A | 12/1965 | Guttman |

(Continued)

FOREIGN PATENT DOCUMENTS

| DE | 202012006191 U1 | 7/2012 |
| EP | 0653220 A1 | 5/1995 |

(Continued)

OTHER PUBLICATIONS

PCT/US2022/039614 filed Aug. 5, 2022 International Search Report and Written Opinion dated Dec. 22, 2022.
(Continued)

*Primary Examiner* — Nathan R Price
*Assistant Examiner* — Kayla M. Turkowski
(74) *Attorney, Agent, or Firm* — Rutan & Tucker LLP (57) ABSTRACT

Elongate blood flash flow paths can be detrimental to the operation of catheter placement systems by delaying the indication time, reducing the efficacy of the vacuum, or increasing the chance of clotting. Catheter placement systems with reduced blood flash fluid paths include blood flash indicators having a proximally slidable syringe barrel and plunger that is fixedly attached to the system housing. By reversing the operation of the blood flash indicator syringe, the clinician maintains the advantages of a visual and tactile feedback while shortening the blood flow path between the needle tip and syringe barrel. Catheter placement systems also include a needle interface structure configured to further shorten the blood flash fluid path.

10 Claims, 6 Drawing Sheets

(58) Field of Classification Search
CPC ........ A61M 5/3148; A61M 2005/3112; A51M 2005/3112; A61B 5/15
See application file for complete search history.

(56) References Cited

U.S. PATENT DOCUMENTS

| | | | |
|---|---|---|---|
| 3,382,872 A | 5/1968 | Rubin | |
| 3,570,485 A | 3/1971 | Reilly | |
| 3,890,976 A | 6/1975 | Bazell et al. | |
| 4,205,675 A | 6/1980 | Vaillancourt | |
| 4,292,970 A | 10/1981 | Hession, Jr. | |
| 4,468,224 A | 8/1984 | Enzmann et al. | |
| 4,525,157 A | 6/1985 | Vaillancourt | |
| 4,581,019 A | 4/1986 | Curelaru et al. | |
| 4,594,073 A | 6/1986 | Stine | |
| 4,702,735 A | 10/1987 | Luther et al. | |
| 4,743,265 A | 5/1988 | Whitehouse et al. | |
| 4,766,908 A | 8/1988 | Clement | |
| 4,863,432 A | 9/1989 | Kvalo | |
| 4,935,008 A | 6/1990 | Lewis, Jr. | |
| 4,950,252 A | 8/1990 | Luther et al. | |
| 4,994,040 A | 2/1991 | Cameron et al. | |
| 5,017,259 A | 5/1991 | Kohsai | |
| 5,040,548 A | 8/1991 | Yock | |
| 5,057,073 A | 10/1991 | Martin | |
| 5,112,312 A | 5/1992 | Luther | |
| 5,115,816 A | 5/1992 | Lee | |
| 5,120,317 A | 6/1992 | Luther | |
| 5,158,544 A | 10/1992 | Weinstein | |
| 5,188,593 A | 2/1993 | Martin | |
| 5,195,962 A | 3/1993 | Martin et al. | |
| 5,207,650 A | 5/1993 | Martin | |
| RE34,416 E | 10/1993 | Lemieux | |
| 5,267,958 A | 12/1993 | Buchbinder et al. | |
| 5,295,970 A | 3/1994 | Clinton et al. | |
| 5,306,247 A | 4/1994 | Pfenninger | |
| 5,312,361 A * | 5/1994 | Zadini .................. | A61M 5/158 604/233 |
| 5,322,512 A | 6/1994 | Mohiuddin | |
| 5,328,472 A | 7/1994 | Steinke et al. | |
| 5,350,358 A | 9/1994 | Martin | |
| 5,358,495 A | 10/1994 | Lynn | |
| 5,368,567 A | 11/1994 | Lee | |
| 5,378,230 A | 1/1995 | Mahurkar | |
| 5,380,290 A | 1/1995 | Makower et al. | |
| 5,389,087 A | 2/1995 | Miraki | |
| 5,439,449 A | 8/1995 | Mapes et al. | |
| 5,443,457 A | 8/1995 | Ginn et al. | |
| 5,460,185 A | 10/1995 | Johnson et al. | |
| 5,489,271 A | 2/1996 | Andersen | |
| 5,573,520 A | 11/1996 | Schwartz et al. | |
| 5,683,370 A | 11/1997 | Luther et al. | |
| 5,713,876 A | 2/1998 | Bogert et al. | |
| 5,718,678 A | 2/1998 | Fleming, III | |
| 5,772,636 A | 6/1998 | Brimhall et al. | |
| 5,885,251 A | 3/1999 | Luther | |
| 5,919,164 A | 7/1999 | Andersen | |
| 5,921,971 A | 7/1999 | Agro et al. | |
| 5,947,940 A | 9/1999 | Beisel | |
| 5,957,893 A | 9/1999 | Luther et al. | |
| 5,971,957 A | 10/1999 | Luther et al. | |
| 6,159,198 A | 12/2000 | Gardeski et al. | |
| 6,206,849 B1 | 3/2001 | Martin et al. | |
| 6,228,062 B1 | 5/2001 | Howell et al. | |
| 6,475,187 B1 | 11/2002 | Gerberding | |
| 6,551,284 B1 | 4/2003 | Greenberg et al. | |
| 6,606,515 B1 | 8/2003 | Windheuser et al. | |
| 6,616,630 B1 | 9/2003 | Woehr et al. | |
| 6,626,869 B1 | 9/2003 | Bint | |
| 6,638,252 B2 | 10/2003 | Moulton et al. | |
| 6,716,228 B2 | 4/2004 | Tal | |
| 6,726,659 B1 | 4/2004 | Stocking et al. | |
| 6,819,951 B2 | 11/2004 | Patel et al. | |
| 6,821,287 B1 | 11/2004 | Jang | |
| 6,926,692 B2 | 8/2005 | Katoh et al. | |
| 6,962,575 B2 | 11/2005 | Tal | |
| 6,991,625 B1 | 1/2006 | Gately et al. | |
| 6,994,693 B2 | 2/2006 | Tal | |
| 6,999,809 B2 | 2/2006 | Currier et al. | |
| 7,025,746 B2 | 4/2006 | Tal | |
| 7,029,467 B2 | 4/2006 | Currier et al. | |
| 7,037,293 B2 | 5/2006 | Carrillo et al. | |
| 7,074,231 B2 | 7/2006 | Jang | |
| 7,094,222 B1 * | 8/2006 | Siekas .................. | B01L 3/0206 604/191 |
| 7,141,050 B2 | 11/2006 | Deal et al. | |
| 7,144,386 B2 | 12/2006 | Korkor et al. | |
| 7,311,697 B2 | 12/2007 | Osborne | |
| 7,364,566 B2 | 4/2008 | Elkins et al. | |
| 7,377,910 B2 | 5/2008 | Katoh et al. | |
| 7,390,323 B2 | 6/2008 | Jang | |
| D600,793 S | 9/2009 | Bierman et al. | |
| D601,242 S | 9/2009 | Bierman et al. | |
| D601,243 S | 9/2009 | Bierman et al. | |
| 7,594,911 B2 | 9/2009 | Powers et al. | |
| 7,691,093 B2 | 4/2010 | Brimhall | |
| 7,722,567 B2 | 5/2010 | Tal | |
| D617,893 S | 6/2010 | Bierman et al. | |
| D624,643 S | 9/2010 | Bierman et al. | |
| 7,819,889 B2 | 10/2010 | Healy et al. | |
| 7,857,788 B2 | 12/2010 | Racz | |
| D630,729 S | 1/2011 | Bierman et al. | |
| 7,909,797 B2 | 3/2011 | Kennedy, II et al. | |
| 7,909,811 B2 | 3/2011 | Agro et al. | |
| 7,922,696 B2 | 4/2011 | Tal et al. | |
| 7,938,820 B2 | 5/2011 | Webster et al. | |
| 7,967,834 B2 | 6/2011 | Tal et al. | |
| 7,976,511 B2 | 7/2011 | Fojtik | |
| 7,985,204 B2 | 7/2011 | Katoh et al. | |
| 8,073,517 B1 | 12/2011 | Burchman | |
| 8,105,286 B2 | 1/2012 | Anderson et al. | |
| 8,192,402 B2 | 6/2012 | Anderson et al. | |
| 8,202,251 B2 | 6/2012 | Bierman et al. | |
| 8,206,356 B2 | 6/2012 | Katoh et al. | |
| 8,361,011 B2 | 1/2013 | Mendels | |
| 8,372,107 B2 | 2/2013 | Tupper | |
| 8,377,006 B2 | 2/2013 | Tal et al. | |
| 8,454,577 B2 | 6/2013 | Joergensen et al. | |
| 8,585,858 B2 | 11/2013 | Kronfeld et al. | |
| 8,657,790 B2 | 2/2014 | Tal et al. | |
| 8,672,888 B2 | 3/2014 | Tal | |
| 8,696,645 B2 | 4/2014 | Tal et al. | |
| 8,784,362 B2 | 7/2014 | Boutilette et al. | |
| 8,827,958 B2 | 9/2014 | Bierman et al. | |
| 8,876,704 B2 | 11/2014 | Golden et al. | |
| 8,882,713 B1 | 11/2014 | Call et al. | |
| 8,900,192 B2 | 12/2014 | Anderson et al. | |
| 8,900,207 B2 | 12/2014 | Uretsky | |
| 8,915,884 B2 | 12/2014 | Tal et al. | |
| 8,956,327 B2 | 2/2015 | Bierman et al. | |
| 9,023,093 B2 | 5/2015 | Pal | |
| 9,067,023 B2 | 6/2015 | Bertocci | |
| 9,126,012 B2 | 9/2015 | McKinnon et al. | |
| 9,138,252 B2 | 9/2015 | Bierman et al. | |
| 9,180,275 B2 | 11/2015 | Helm | |
| 9,265,920 B2 | 2/2016 | Rundquist et al. | |
| 9,272,121 B2 | 3/2016 | Piccagli | |
| 9,445,734 B2 | 9/2016 | Grunwald | |
| 9,522,254 B2 | 12/2016 | Belson | |
| 9,554,785 B2 | 1/2017 | Walters et al. | |
| 9,566,087 B2 | 2/2017 | Bierman et al. | |
| 9,675,784 B2 | 6/2017 | Belson | |
| 9,713,695 B2 | 7/2017 | Bunch et al. | |
| 9,764,117 B2 | 9/2017 | Bierman et al. | |
| 9,770,573 B2 | 9/2017 | Golden et al. | |
| 9,814,861 B2 | 11/2017 | Boutilette et al. | |
| 9,820,845 B2 | 11/2017 | von Lehe et al. | |
| 9,861,383 B2 | 1/2018 | Clark | |
| 9,872,971 B2 | 1/2018 | Blanchard | |
| 9,884,169 B2 | 2/2018 | Bierman et al. | |
| 9,889,275 B2 | 2/2018 | Voss et al. | |
| 9,913,585 B2 | 3/2018 | McCaffrey et al. | |
| 9,913,962 B2 | 3/2018 | Tal et al. | |
| 9,981,113 B2 | 5/2018 | Bierman | |

(56) References Cited

U.S. PATENT DOCUMENTS

| | | |
|---|---|---|
| 10,010,312 B2 | 7/2018 | Tegels |
| 10,065,020 B2 | 9/2018 | Gaur |
| 10,086,170 B2 | 10/2018 | Chhikara et al. |
| 10,098,724 B2 | 10/2018 | Adams et al. |
| 10,111,683 B2 | 10/2018 | Tsamir et al. |
| 10,118,020 B2 | 11/2018 | Avneri et al. |
| 10,130,269 B2 | 11/2018 | McCaffrey et al. |
| 10,220,184 B2 | 3/2019 | Clark |
| 10,220,191 B2 | 3/2019 | Belson et al. |
| 10,265,508 B2 | 4/2019 | Baid |
| 10,271,873 B2 | 4/2019 | Steingisser et al. |
| 10,376,675 B2 | 8/2019 | Mitchell et al. |
| 10,675,440 B2 | 6/2020 | Abitabilo et al. |
| 10,688,281 B2 | 6/2020 | Blanchard et al. |
| 10,806,901 B2 | 10/2020 | Burkholz et al. |
| 10,926,060 B2 | 2/2021 | Stern et al. |
| 11,260,206 B2 | 3/2022 | Stone et al. |
| 11,400,260 B2 | 8/2022 | Huang et al. |
| 11,759,607 B1 | 9/2023 | Biancarelli |
| 2002/0040231 A1 | 4/2002 | Wysoki |
| 2002/0198492 A1 | 12/2002 | Miller et al. |
| 2003/0036712 A1 | 2/2003 | Heh et al. |
| 2003/0060863 A1 | 3/2003 | Dobak |
| 2003/0088212 A1 | 5/2003 | Tal |
| 2003/0100849 A1 | 5/2003 | Jang |
| 2003/0153874 A1 | 8/2003 | Tal |
| 2003/0158514 A1 | 8/2003 | Tal |
| 2004/0015138 A1 | 1/2004 | Currier et al. |
| 2004/0064086 A1 | 4/2004 | Gottlieb et al. |
| 2004/0116864 A1 | 6/2004 | Boudreaux |
| 2004/0116901 A1 | 6/2004 | Appling |
| 2004/0167478 A1 | 8/2004 | Mooney et al. |
| 2004/0193093 A1 | 9/2004 | Desmond |
| 2004/0230178 A1 | 11/2004 | Wu |
| 2005/0004554 A1 | 1/2005 | Osborne |
| 2005/0120523 A1 | 6/2005 | Schweikert |
| 2005/0131343 A1 | 6/2005 | Abrams et al. |
| 2005/0215956 A1 | 9/2005 | Nerney |
| 2005/0245882 A1 | 11/2005 | Elkins et al. |
| 2005/0283221 A1 | 12/2005 | Mann et al. |
| 2006/0009740 A1 | 1/2006 | Higgins et al. |
| 2006/0116629 A1 | 6/2006 | Tal et al. |
| 2006/0129100 A1 | 6/2006 | Tal |
| 2006/0129130 A1 | 6/2006 | Tal et al. |
| 2007/0276288 A1 | 11/2007 | Khaw |
| 2008/0045894 A1 | 2/2008 | Perchik et al. |
| 2008/0125744 A1 | 5/2008 | Treacy |
| 2008/0125748 A1 | 5/2008 | Patel |
| 2008/0132850 A1 | 6/2008 | Fumiyama et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0312578 A1 | 12/2008 | DeFonzo et al. |
| 2008/0319387 A1 | 12/2008 | Amisar et al. |
| 2009/0187147 A1 | 7/2009 | Kurth et al. |
| 2009/0221961 A1 | 9/2009 | Tal et al. |
| 2009/0270889 A1 | 10/2009 | Tal et al. |
| 2009/0292272 A1 | 11/2009 | McKinnon |
| 2010/0030154 A1 | 2/2010 | Duffy |
| 2010/0256487 A1 | 10/2010 | Hawkins et al. |
| 2010/0298839 A1 | 11/2010 | Castro |
| 2010/0305474 A1 | 12/2010 | DeMars et al. |
| 2011/0004162 A1 | 1/2011 | Tal |
| 2011/0009827 A1 | 1/2011 | Bierman et al. |
| 2011/0021994 A1 | 1/2011 | Anderson et al. |
| 2011/0066142 A1 | 3/2011 | Tal et al. |
| 2011/0071502 A1 | 3/2011 | Asai |
| 2011/0144620 A1 | 6/2011 | Tal |
| 2011/0152836 A1 | 6/2011 | Riopelle et al. |
| 2011/0190778 A1 | 8/2011 | Arpasi et al. |
| 2011/0202006 A1 | 8/2011 | Bierman et al. |
| 2011/0251559 A1 | 10/2011 | Tal et al. |
| 2011/0270192 A1 | 11/2011 | Anderson et al. |
| 2012/0041371 A1 | 2/2012 | Tal et al. |
| 2012/0065590 A1 | 3/2012 | Bierman et al. |
| 2012/0078231 A1 | 3/2012 | Hoshinouchi |
| 2012/0130411 A1 | 5/2012 | Tal et al. |
| 2012/0130415 A1 | 5/2012 | Tal et al. |
| 2012/0157854 A1 | 6/2012 | Kurrus et al. |
| 2012/0215171 A1 | 8/2012 | Christiansen |
| 2012/0220942 A1 | 8/2012 | Hall et al. |
| 2012/0226239 A1 | 9/2012 | Green |
| 2012/0283640 A1 | 11/2012 | Anderson et al. |
| 2012/0316500 A1 | 12/2012 | Bierman et al. |
| 2013/0053763 A1 | 2/2013 | Makino et al. |
| 2013/0053826 A1 | 2/2013 | Shevgoor |
| 2013/0123704 A1 | 5/2013 | Bierman et al. |
| 2013/0158338 A1 | 6/2013 | Kelly et al. |
| 2013/0188291 A1 | 7/2013 | Vardiman |
| 2013/0237931 A1 | 9/2013 | Tal et al. |
| 2013/0306079 A1 | 11/2013 | Tracy |
| 2014/0025036 A1 | 1/2014 | Bierman et al. |
| 2014/0081210 A1 | 3/2014 | Bierman et al. |
| 2014/0094774 A1 | 4/2014 | Blanchard |
| 2014/0100552 A1 | 4/2014 | Gallacher et al. |
| 2014/0207052 A1 | 7/2014 | Tal et al. |
| 2014/0207069 A1 | 7/2014 | Bierman et al. |
| 2014/0214005 A1 | 7/2014 | Belson |
| 2014/0257111 A1 | 9/2014 | Yamashita et al. |
| 2014/0276432 A1 | 9/2014 | Bierman et al. |
| 2014/0276599 A1 | 9/2014 | Cully et al. |
| 2015/0011834 A1 | 1/2015 | Ayala et al. |
| 2015/0080939 A1 | 3/2015 | Adams et al. |
| 2015/0094653 A1 | 4/2015 | Pacheco et al. |
| 2015/0112307 A1 | 4/2015 | Margolis |
| 2015/0112310 A1 | 4/2015 | Call et al. |
| 2015/0126930 A1 | 5/2015 | Bierman et al. |
| 2015/0148595 A1 | 5/2015 | Bagwell et al. |
| 2015/0190168 A1 | 7/2015 | Bierman et al. |
| 2015/0196210 A1 | 7/2015 | McCaffrey et al. |
| 2015/0224287 A1 | 8/2015 | Bian et al. |
| 2015/0231364 A1 | 8/2015 | Blanchard et al. |
| 2015/0283357 A1 | 10/2015 | Lampropoulos et al. |
| 2015/0297868 A1 | 10/2015 | Tal et al. |
| 2015/0320969 A1 | 11/2015 | Haslinger et al. |
| 2015/0320977 A1 | 11/2015 | Vitullo et al. |
| 2015/0351793 A1 | 12/2015 | Bierman et al. |
| 2015/0359549 A1 | 12/2015 | Lenker et al. |
| 2015/0359998 A1 | 12/2015 | Carmel et al. |
| 2016/0082223 A1 | 3/2016 | Barnell |
| 2016/0114124 A1 | 4/2016 | Tal |
| 2016/0158523 A1 | 6/2016 | Helm |
| 2016/0220786 A1 | 8/2016 | Mitchell et al. |
| 2016/0242661 A1 | 8/2016 | Fischell et al. |
| 2016/0256101 A1 | 9/2016 | Aharoni et al. |
| 2016/0325073 A1 | 11/2016 | Davies et al. |
| 2016/0331938 A1 | 11/2016 | Blanchard et al. |
| 2016/0338728 A1 | 11/2016 | Tal |
| 2016/0346503 A1 | 12/2016 | Jackson et al. |
| 2017/0035990 A1 | 2/2017 | Swift |
| 2017/0072165 A1 | 3/2017 | Lim et al. |
| 2017/0120000 A1 | 5/2017 | Osypka et al. |
| 2017/0120014 A1 | 5/2017 | Harding et al. |
| 2017/0120034 A1 | 5/2017 | Kaczorowski |
| 2017/0128700 A1 | 5/2017 | Roche Rebollo |
| 2017/0156987 A1 | 6/2017 | Babbs et al. |
| 2017/0172653 A1 | 6/2017 | Urbanski et al. |
| 2017/0182293 A1* | 6/2017 | Chhikara .......... A61M 25/0606 |
| 2017/0239443 A1 | 8/2017 | Abitabilo et al. |
| 2017/0259043 A1 | 9/2017 | Chan et al. |
| 2017/0273713 A1 | 9/2017 | Shah et al. |
| 2017/0296792 A1 | 10/2017 | Ornelas Vargas et al. |
| 2017/0326339 A1 | 11/2017 | Bailey et al. |
| 2017/0361070 A1 | 12/2017 | Hivert |
| 2017/0368255 A1 | 12/2017 | Provost et al. |
| 2018/0001062 A1 | 1/2018 | O'Carrol et al. |
| 2018/0021545 A1 | 1/2018 | Mitchell et al. |
| 2018/0116690 A1 | 5/2018 | Sarabia et al. |
| 2018/0117284 A1 | 5/2018 | Appling et al. |
| 2018/0133438 A1 | 5/2018 | Hulvershorn et al. |
| 2018/0154062 A1 | 6/2018 | DeFonzo et al. |
| 2018/0154112 A1 | 6/2018 | Chan et al. |
| 2018/0214674 A1 | 8/2018 | Ebnet et al. |
| 2018/0296799 A1 | 10/2018 | Horst et al. |

(56) References Cited

U.S. PATENT DOCUMENTS

| | | |
|---|---|---|
| 2018/0296804 A1 | 10/2018 | Bierman |
| 2018/0310955 A1 | 11/2018 | Lindekugel et al. |
| 2019/0015646 A1 | 1/2019 | Matlock et al. |
| 2019/0021640 A1 | 1/2019 | Burkholz et al. |
| 2019/0060616 A1 | 2/2019 | Solomon |
| 2019/0076167 A1 | 3/2019 | Fantuzzi et al. |
| 2019/0134349 A1 | 5/2019 | Cohn et al. |
| 2019/0192824 A1 | 6/2019 | Cordeiro et al. |
| 2019/0201665 A1 | 7/2019 | Turpin |
| 2019/0209812 A1 | 7/2019 | Burkholz et al. |
| 2019/0255294 A1 | 8/2019 | Mitchell et al. |
| 2019/0255298 A1 | 8/2019 | Mitchell et al. |
| 2019/0275303 A1 | 9/2019 | Tran et al. |
| 2019/0276268 A1 | 9/2019 | Akingba |
| 2019/0321590 A1 | 10/2019 | Burkholz et al. |
| 2019/0351196 A1 | 11/2019 | Ribelin et al. |
| 2020/0001051 A1 | 1/2020 | Huang et al. |
| 2020/0016374 A1 | 1/2020 | Burkholz et al. |
| 2020/0046948 A1 | 2/2020 | Burkholz et al. |
| 2020/0100716 A1 | 4/2020 | Devgon et al. |
| 2020/0129732 A1 | 4/2020 | Vogt et al. |
| 2020/0147349 A1 | 5/2020 | Holt |
| 2020/0197682 A1 | 6/2020 | Franklin et al. |
| 2020/0197684 A1 | 6/2020 | Wax |
| 2020/0237278 A1 | 7/2020 | Asbaghi |
| 2020/0359995 A1 | 11/2020 | Walsh et al. |
| 2021/0030944 A1 | 2/2021 | Cushen et al. |
| 2021/0060306 A1* | 3/2021 | Kumar ............... A61M 25/0606 |
| 2021/0069471 A1 | 3/2021 | Howell |
| 2021/0085927 A1 | 3/2021 | Howell |
| 2021/0100985 A1 | 4/2021 | Akcay et al. |
| 2021/0113809 A1 | 4/2021 | Howell |
| 2021/0113810 A1 | 4/2021 | Howell |
| 2021/0113816 A1 | 4/2021 | DiCianni |
| 2021/0121661 A1 | 4/2021 | Howell |
| 2021/0121667 A1 | 4/2021 | Howell |
| 2021/0228842 A1 | 7/2021 | Scherich et al. |
| 2021/0228843 A1 | 7/2021 | Howell et al. |
| 2021/0244920 A1 | 8/2021 | Kujawa et al. |
| 2021/0290898 A1 | 9/2021 | Burkholz |
| 2021/0290901 A1 | 9/2021 | Burkholz et al. |
| 2021/0290913 A1 | 9/2021 | Horst et al. |
| 2021/0322729 A1 | 10/2021 | Howell |
| 2021/0330941 A1 | 10/2021 | Howell et al. |
| 2021/0330942 A1 | 10/2021 | Howell |
| 2021/0361915 A1 | 11/2021 | Howell et al. |
| 2021/0402149 A1 | 12/2021 | Howell |
| 2021/0402153 A1 | 12/2021 | Howell et al. |
| 2022/0001138 A1 | 1/2022 | Howell |
| 2022/0032013 A1 | 2/2022 | Howell et al. |
| 2022/0032014 A1 | 2/2022 | Howell et al. |
| 2022/0062528 A1 | 3/2022 | Thornley et al. |
| 2022/0062596 A1 | 3/2022 | Ribelin et al. |
| 2022/0126064 A1 | 4/2022 | Tobin et al. |
| 2022/0193376 A1 | 6/2022 | Spataro et al. |
| 2022/0193377 A1 | 6/2022 | Haymond et al. |
| 2022/0323723 A1 | 10/2022 | Spataro et al. |
| 2022/0331562 A1 | 10/2022 | Jaros et al. |
| 2022/0331563 A1 | 10/2022 | Papadia |
| 2023/0042898 A1 | 2/2023 | Howell et al. |
| 2023/0096377 A1 | 3/2023 | West et al. |
| 2023/0096740 A1 | 3/2023 | Bechstein et al. |
| 2023/0099654 A1 | 3/2023 | Blanchard et al. |
| 2023/0100482 A1 | 3/2023 | Howell |
| 2023/0101455 A1 | 3/2023 | Howell et al. |
| 2023/0102231 A1 | 3/2023 | Bechstein et al. |
| 2023/0173231 A1 | 6/2023 | Parikh et al. |
| 2023/0233814 A1 | 7/2023 | Howell et al. |
| 2023/0381459 A1 | 11/2023 | Belson et al. |
| 2024/0009427 A1 | 1/2024 | Howell et al. |
| 2024/0050706 A1 | 2/2024 | Howell et al. |
| 2024/0198058 A1 | 6/2024 | Howell et al. |
| 2025/0001136 A1 | 1/2025 | Mitchell et al. |

FOREIGN PATENT DOCUMENTS

| | | |
|---|---|---|
| EP | 0730880 A1 | 9/1996 |
| EP | 2061385 A1 | 5/2009 |
| EP | 1458437 B1 | 3/2010 |
| EP | 2248549 A2 | 11/2010 |
| EP | 2319576 A1 | 5/2011 |
| EP | 2366422 A1 | 9/2011 |
| EP | 2486880 A2 | 8/2012 |
| EP | 2486881 A2 | 8/2012 |
| EP | 2486951 A2 | 8/2012 |
| EP | 2512576 A2 | 10/2012 |
| EP | 2152348 B1 | 2/2015 |
| EP | 3473291 A1 | 4/2019 |
| EP | 3093038 B1 | 5/2019 |
| EP | 2260897 B1 | 9/2019 |
| EP | 3693051 A1 | 8/2020 |
| GB | 1273547 A | 5/1972 |
| JP | 2004248987 A | 9/2004 |
| JP | 2008054859 A | 3/2008 |
| WO | 94/21315 A1 | 9/1994 |
| WO | 95/32009 A2 | 11/1995 |
| WO | 98/44979 A1 | 10/1998 |
| WO | 98/53871 A1 | 12/1998 |
| WO | 9857685 A1 | 12/1998 |
| WO | 99/12600 A1 | 3/1999 |
| WO | 99/26681 A1 | 6/1999 |
| WO | 00/06221 A1 | 2/2000 |
| WO | 0054830 A1 | 9/2000 |
| WO | 2003008020 A1 | 1/2003 |
| WO | 2003057272 A2 | 7/2003 |
| WO | 03/068073 A1 | 8/2003 |
| WO | 2003066125 A2 | 8/2003 |
| WO | 2005096778 A2 | 10/2005 |
| WO | 2006055288 A2 | 5/2006 |
| WO | 2006055780 A2 | 5/2006 |
| WO | 2007046850 A2 | 4/2007 |
| WO | 2008033983 A1 | 3/2008 |
| WO | 2008092029 A2 | 7/2008 |
| WO | 2008/131300 A2 | 10/2008 |
| WO | 2008131289 A2 | 10/2008 |
| WO | 2009114833 A1 | 9/2009 |
| WO | 2009114837 A2 | 9/2009 |
| WO | 2010/048449 A2 | 4/2010 |
| WO | 2010056906 A2 | 5/2010 |
| WO | 2010083467 A2 | 7/2010 |
| WO | 2010/132608 A2 | 11/2010 |
| WO | 2011081859 A2 | 7/2011 |
| WO | 2011097639 A2 | 8/2011 |
| WO | 2011109792 A1 | 9/2011 |
| WO | 2011146764 A1 | 11/2011 |
| WO | 2012068162 A2 | 5/2012 |
| WO | 2012068166 A2 | 5/2012 |
| WO | 2012135761 A1 | 10/2012 |
| WO | 2012/154277 A1 | 11/2012 |
| WO | 2012162677 A1 | 11/2012 |
| WO | 2013026045 A1 | 2/2013 |
| WO | 2013138519 A2 | 9/2013 |
| WO | 2014006403 A1 | 1/2014 |
| WO | 2014/100392 A1 | 6/2014 |
| WO | 2014113257 A2 | 7/2014 |
| WO | 2014152005 A2 | 9/2014 |
| WO | 2014197614 A2 | 12/2014 |
| WO | 2015057766 A1 | 4/2015 |
| WO | 2015077560 A1 | 5/2015 |
| WO | 2015/168655 A2 | 11/2015 |
| WO | 2016110824 A1 | 7/2016 |
| WO | 2016123278 A1 | 8/2016 |
| WO | 2016139590 A1 | 9/2016 |
| WO | 2016139597 A2 | 9/2016 |
| WO | 2016/178974 A1 | 11/2016 |
| WO | 2016/187063 A1 | 11/2016 |
| WO | 2016176065 A1 | 11/2016 |
| WO | 2018089275 A1 | 5/2018 |
| WO | 2018089285 A1 | 5/2018 |
| WO | 2018089385 A1 | 5/2018 |
| WO | 2018191547 A1 | 10/2018 |
| WO | 2018213148 A1 | 11/2018 |
| WO | 2018218236 A1 | 11/2018 |

(56) References Cited

FOREIGN PATENT DOCUMENTS

| | | |
|---|---|---|
| WO | 2019/050576 A1 | 3/2019 |
| WO | 2019/146026 A1 | 8/2019 |
| WO | 2019199734 A1 | 10/2019 |
| WO | 2020014149 A1 | 1/2020 |
| WO | 2020069395 A1 | 4/2020 |
| WO | 2020/109448 A1 | 6/2020 |
| WO | 2020/113123 A1 | 6/2020 |
| WO | 2021038041 A1 | 3/2021 |
| WO | 2021050302 A1 | 3/2021 |
| WO | 2021/077103 A1 | 4/2021 |
| WO | 2021062023 A1 | 4/2021 |
| WO | 2021081205 A1 | 4/2021 |
| WO | 2021086793 A1 | 5/2021 |
| WO | 2021/236950 A1 | 11/2021 |
| WO | 2021226050 A1 | 11/2021 |
| WO | 2022/031618 A1 | 2/2022 |
| WO | 2022/094141 A1 | 5/2022 |
| WO | 2022/133297 A1 | 6/2022 |
| WO | 2022-140406 A1 | 6/2022 |
| WO | 2022/140429 A1 | 6/2022 |
| WO | 2022/217098 A1 | 10/2022 |
| WO | 2023014994 A1 | 2/2023 |
| WO | 2023049498 A1 | 3/2023 |
| WO | 2023049505 A1 | 3/2023 |
| WO | 2023049511 A1 | 3/2023 |
| WO | 2023049519 A1 | 3/2023 |
| WO | 2023049522 A1 | 3/2023 |
| WO | 2023146792 A1 | 8/2023 |

OTHER PUBLICATIONS

PCT/US2022/044848 filed Sep. 27, 2022 International Search Report and Written Opinion dated Feb. 3, 2023.
PCT/US2022/044879 filed Sep. 27, 2022 International Search Report and Written Opinion dated Mar. 3, 2023.
PCT/US2022/044901 filed Sep. 27, 2022 International Search Report and Written Opinion dated Mar. 3, 2023.
PCT/US2022/044918 filed Sep. 27, 2022 International Search Report and Written Opinion dated Feb. 21, 2023.
PCT/US2022/044923 filed Sep. 27, 2022 International Search Report and Written Opinion dated Feb. 15, 2023.
U.S. Appl. No. 17/156,252, filed Jan. 22, 2021 Notice of Allowance dated Apr. 24, 2023.
U.S. Appl. No. 17/237,909, filed Apr. 22, 2021 Restriction Requirement dated Feb. 1, 2023.
U.S. Appl. No. 17/326,017, filed May 20, 2021 Non-Final Office Action dated Jan. 26, 2023.
U.S. Appl. No. 17/390,682, filed Jul. 30, 2021 Non-Final Office Action dated Mar. 2, 2023.
U.S. Appl. No. 17/392,061, filed Aug. 2, 2021 Restriction Requirement dated Mar. 30, 2023.
PCT/US2020/052536 filed Sep. 24, 2020 International Search Report and Written Opinion dated Dec. 4, 2020.
PCT/US2021/014700 filed Jan. 22, 2021 International Search Report and Written Opinion dated Jun. 29, 2021.
PCT/US2021/028018 filed Apr. 19, 2021 International Search Report and Written Opinion dated Sep. 13, 2021.
PCT/US2021/028683 filed Apr. 22, 2021 International Search Report and Written Opinion dated Sep. 16, 2021.
PCT/US2021/029183 filed Apr. 26, 2021 International Search Report and Written Opinion dated Sep. 24, 2021.
PCT/US2021/033443 filed May 20, 2021 International Search Report and Written Opinion dated Sep. 23, 2021.
PCT/US2021/039084 filed Jun. 25, 2021 International Search Report and Written Opinion dated Jan. 10, 2022.
PCT/US2021/044029 filed Jul. 30, 2021 International Search Report and Written Opinion dated Dec. 9, 2021.
PCT/US2021/044223 filed Aug. 2, 2021 International Search Report and Written Opinion dated Dec. 21, 2021.
PCT/US2021/048275 filed Aug. 30, 2021 International Search Report and Written Opinion dated Jan. 4, 2022.
U.S. Appl. No. 15/008,628, filed Jan. 28, 2016 Final Office Action dated May 30, 2018.
U.S. Appl. No. 15/008,628, filed Jan. 28, 2016 Non-Final Office Action dated Jan. 25, 2019.
U.S. Appl. No. 15/008,628, filed Jan. 28, 2016 Non-Final Office Action dated Nov. 2, 2017.
U.S. Appl. No. 15/008,628, filed Jan. 28, 2016 Notice of Allowance dated May 15, 2019.
U.S. Appl. No. 16/398,020, filed Apr. 29, 2019 Final Office Action dated Jan. 25, 2022.
U.S. Appl. No. 16/398,020, filed Apr. 29, 2019 Non-Final Office Action dated May 11, 2021.
U.S. Appl. No. 17/031,478, filed Sep. 24, 2020 Non-Final Office Action dated May 11, 2022.
PCT/US2021/057135 filed Oct. 28, 2021 International Preliminary Report on Patentability dated May 2, 2023.
PCT/US2021/057135 filed Oct. 28, 2021 International Search Report and Written Opinion dated Mar. 11, 2022.
PCT/US2023/011173 filed Jan. 19, 2023 International Search Report and Written Opinion dated May 22, 2023.
U.S. Appl. No. 17/240,591, filed Apr. 26, 2021 Non-Final Office Action dated Jun. 8, 2023.
U.S. Appl. No. 17/326,017, filed May 20, 2021 Notice of Allowance dated Jul. 3, 2023.
U.S. Appl. No. 17/358,504, filed Jun. 25, 2021 Restriction Requirement dated Jun. 7, 2023.
U.S. Appl. No. 17/360,694, filed Jun. 28, 2021 Restriction Requirement dated Jul. 20, 2023.
U.S. Appl. No. 17/392,061, filed Aug. 2, 2021 Non-Final Office Action dated Jul. 17, 2023.
PCT/US2021/028018 filed Apr. 19, 2021 International Preliminary Report on Patentability dated Jun. 3, 2022.
PCT/US2021/064174 filed Dec. 17, 2021 International Search Report and Written Opinion dated May 18, 2022.
PCT/US2021/064642 filed Dec. 21, 2021 International Search Report and Written Opinion dated May 11, 2022.
PCT/US2021/064671 filed Dec. 21, 2021 International Search Report and Written Opinion dated May 27, 2022.
PCT/US2022/024085 filed Apr. 8, 2022 International Search Report and Wirtten Opinion dated Sep. 12, 2022.
U.S. Appl. No. 16/398,020, filed Apr. 29, 2019 Examiner's Answer dated Oct. 31, 2022.
U.S. Appl. No. 17/031,478, filed Sep. 24, 2020 Notice of Allowance dated Sep. 16, 2022.
U.S. Appl. No. 17/156,252, filed Jan. 22, 2021 Non-Final Office Action dated Oct. 25, 2022.
U.S. Appl. No. 16/398,020, filed Apr. 29, 2019 Board Decision dated Oct. 30, 2023.
U.S. Appl. No. 16/398,020, filed Apr. 29, 2019 Non-Final Office Action dated Jan. 18, 2024.
U.S. Appl. No. 17/234,611, filed Apr. 19, 2021 Restriction Requirement dated Jan. 18, 2024.
U.S. Appl. No. 17/237,909, filed Apr. 22, 2021 Notice of Allowance dated Oct. 27, 2023.
U.S. Appl. No. 17/240,591, filed Apr. 26, 2021 Final Office Action dated Dec. 6, 2023.
U.S. Appl. No. 17/360,694, filed Jun. 28, 2021 Non-Final Office Action dated Feb. 14, 2024.
U.S. Appl. No. 17/390,682, filed Jul. 30, 2021 Non-Final Office Action dated Dec. 1, 2023.
U.S. Appl. No. 17/392,061, filed Aug. 2, 2021 Advisory Action dated Feb. 14, 2024.
U.S. Appl. No. 17/392,061, filed Aug. 2, 2021 Final Office Action dated Nov. 21, 2023.
U.S. Appl. No. 17/513,789, filed Oct. 28, 2021 Non-Final Office Action dated Jan. 9, 2024.
U.S. Appl. No. 17/234,611, filed Apr. 19, 2021 Non-Final Office Action dated Apr. 23, 2024.
U.S. Appl. No. 17/240,591, filed Apr. 26, 2021 Advisory Action dated Feb. 22, 2024.

(56) References Cited

OTHER PUBLICATIONS

U.S. Appl. No. 17/358,504, filed Jun. 25, 2021 Final Office Action dated Mar. 13, 2024.
U.S. Appl. No. 17/390,682, filed Jul. 30, 2021 Final Office Action dated May 6, 2024.
U.S. Appl. No. 17/392,061, filed Aug. 2, 2021 Non-Final Office Action dated Apr. 23, 2024.
U.S. Appl. No. 17/554,978, filed Dec. 17, 2021 Non-Final Office Action dated Apr. 19, 2024.
U.S. Appl. No. 17/156,252, filed Jan. 22, 2021 Notice of Allowance dated Aug. 9, 2023.
U.S. Appl. No. 17/237,909, filed Apr. 22, 2021 Non-Final Office Action dated Jul. 27, 2023.
U.S. Appl. No. 17/358,504, filed Jun. 25, 2021 Non-Final Office Action dated Oct. 4, 2023.
U.S. Appl. No. 17/360,694, filed Jun. 28, 2021 Non-Final Office Action dated Oct. 13, 2023.
U.S. Appl. No. 17/390,682, filed Jul. 30, 2021 Final Office Action dated Jul. 27, 2023.
U.S. Appl. No. 17/513,789, filed Oct. 28, 2021 Restriction Requirement dated Oct. 3, 2023.
U.S. Appl. No. 17/234,611, filed Apr. 19, 2021 Final Office Action dated Sep. 20, 2024.
U.S. Appl. No. 17/240,591, filed Apr. 26, 2021 Final Office Action dated Aug. 14, 2024.
U.S. Appl. No. 17/558,124, filed Dec. 21, 2021 Non-Final Office Action dated Sep. 20, 2024.
U.S. Appl. No. 16/398,020, filed Apr. 29, 2019 Notice of Allowance dated May 20, 2024.
U.S. Appl. No. 17/240,591, filed Apr. 26, 2021 Non-Final Office Action dated Jun. 4, 2024.
U.S. Appl. No. 17/358,504, filed Jun. 25, 2021 Notice of Allowance dated Jul. 17, 2024.
U.S. Appl. No. 17/390,682, filed Jul. 30, 2021 Non-Final Office Action dated Jul. 5, 2024.
U.S. Appl. No. 17/513,789, filed Oct. 28, 2021 Final Office Action dated Jul. 9, 2024.
U.S. Appl. No. 17/554,978, filed Dec. 17, 2021 Notice of Allowance dated Jul. 24, 2024.
U.S. Appl. No. 17/360,694, filed Jun. 28, 2021 Notice of Allowance dated Dec. 16, 2024.
U.S. Appl. No. 17/392,061, filed Aug. 2, 2021 Final Office Action dated Jan. 2, 2025.
U.S. Appl. No. 17/461,619, filed Aug. 30, 2021 Restriction Requirement dated Dec. 6, 2024.
U.S. Appl. No. 17/513,789, filed Oct. 28, 2021 Notice of Allowance dated Jan. 3, 2025.

* cited by examiner

FLUID PATH OPTIMIZATION IN CATHETER INSERTION SYSTEMS

PRIORITY

This application claims the benefit of priority to U.S. Provisional Application No. 63/128,677, filed Dec. 21, 2020, which is incorporated by reference in its entirety into this application.

SUMMARY

Briefly summarized, embodiments disclosed herein are directed to fluid path optimization in catheter insertion systems, and associated methods thereof. When placing elongate catheters, such as central venous catheters (CVC), rapid insertion central catheters (RICC), or the like, advanced insertion systems are desirable. These insertion systems can include housings, needles, guidewires, dilators, or blood flash indicators configured to access the vasculature, confirm correct vascular access, dilate the insertion site and place the catheter. Advantageously, the insertion systems can contain the above structures within an enclosed environment to reduce the repeated insertion and removal of multiple devices, and mitigate the introduction of pathogens.

The sequential nature of the tools within these insertion systems can result in a long and convoluted pathways for the blood flow before reaching the blood flash indicator. For example, a needle disposed within a lumen of the catheter, requires blood to flow to at least a proximal end of the catheter before exiting and being observed. Further, blood flash indicators can be situated towards a distal end of the insertion device, proximate the insertion site for ease of observation. As such the blood flow would have to travel twice the length of the catheter before being observed.

Such elongate flow pathways can lead to various problems. For example, the longer flow path requires increased volumes of blood to flow through the system before reaching the blood flash indicator and being observed. Such elongate flow paths can obscure the nature of the pulsatile flow, obfuscating the difference between arterial or venous flow. The delay caused by the increase travel time can lead to a user continuing with insertion despite having accessed the vasculature, resulting in "backwalling" the vessel, i.e. inserting the needle through a far wall of the vessel. Where blood flash systems include a vacuum to draw the blood flow, the convoluted flow path can reduce or compromise the force of the vacuum. Lastly, elongate blood flow pathways can have an increased risk of the blood clotting prior to reaching the blood flash indicator. Embodiments disclosed herein are directed to resolving the aforementioned problems.

Disclosed herein is a catheter insertion system including, a catheter defining a catheter lumen and extending along a longitudinal axis, a needle defining a needle lumen and disposed within a portion of the catheter lumen, a housing supporting one of the catheter or the needle, and a blood flash indicator in fluid communication with the needle lumen, the blood flash indicator including a plunger fixedly attached to the housing and a syringe barrel slidably engaged with the plunger along the longitudinal axis.

In some embodiments, the syringe barrel is configured to slide proximally relative to one of the plunger or the housing to create a vacuum and draw a blood flow through the needle lumen and into the syringe barrel. The syringe barrel is formed of a transparent material to allow for observation of a blood color or pulsatile flow. The syringe barrel is supported by a cradle including a gripping feature and configured to facilitate sliding of the syringe barrel along the longitudinal axis. The housing includes a needle interface defining a needle channel and a blood flash channel, the needle channel configured to receive a portion of the needle extending therethrough and the blood flash channel providing fluid communication between the needle channel and the syringe barrel.

In some embodiments, the needle includes a notch extending through a wall of the needle to provide fluid communication between the needle lumen and the needle channel. The needle channel includes a first O-ring disposed annularly about the needle and disposed distally of the needle notch, and a second O-ring disposed annularly about the needle and disposed proximally of the needle notch, the first O-ring and the second O-ring each extending between an outer surface of the needle and an inner surface of the needle channel to provide a fluid-tight seal therebetween. The needle is slidably engaged with the needle channel. In some embodiments, a portion of the blood flash channel is formed of a flexible tube. The catheter is a central venous catheter or a rapid insertion central catheter.

Also disclosed is a method placing a catheter including, accessing a vasculature with a needle, defining a needle lumen and supported by a housing, sliding a syringe barrel proximally along a longitudinal axis relative to the housing, creating a vacuum within the syringe barrel, and drawing a blood flow through the needle lumen and into the syringe barrel.

In some embodiments, the method further includes a plunger slidably engaged with the syringe barrel, the plunger fixedly attached to the housing to prevent any relative longitudinal movement therebetween. In some embodiments, the method further includes a cradle coupled with the syringe barrel and including a gripping feature. In some embodiments, the method further includes observing a blood flow color or pulsatile flow within the syringe barrel, the syringe barrel formed of a transparent material. In some embodiments, the housing includes a needle interface defining a needle channel and a blood flash channel, the needle channel configured to receive a portion of the needle extending therethrough and the blood flash channel providing fluid communication between the needle channel and the syringe barrel. The needle includes a notch extending through a wall of the needle to provide fluid communication between the needle lumen and the needle channel.

In some embodiments, the needle channel includes a first O-ring disposed annularly about the needle and disposed distally of the needle notch, and a second O-ring disposed annularly about the needle and disposed proximally of the needle notch, the first O-ring and the second O-ring each extending between an outer surface of the needle and an inner surface of the needle channel to provide a fluid-tight seal therebetween. The needle is slidably engaged with the needle channel. In some embodiments, a portion of the blood flash channel is formed of a flexible tube. The catheter is a central venous catheter or a rapid insertion central catheter.

Also disclosed is a catheter placement system including, a catheter defining a catheter lumen and extending along a longitudinal axis, a needle defining a needle lumen and extending through a portion of the catheter lumen, a housing supporting one or both of the catheter and the needle, and including a needle interface piece to provide fluid communication between the needle lumen and a blood flash channel, and a blood flash indicator in fluid communication with the blood flash channel at a point distal of a proximal end of the needle, the blood flash indicator including a syringe barrel fixedly attached to the housing and a plunger slidably engaged with the syringe barrel between proximal position and a distal position.

In some embodiments, the plunger is configured to slide from the proximal position to the distal position to create a vacuum within the syringe barrel. The needle interface piece defines a needle channel communicating with the blood flash channel, the needle channel configured to receive a portion of the needle extending therethrough. The needle includes a notch extending through a wall of the needle to provide fluid communication between the needle lumen and the needle channel. The needle channel includes a first O-ring disposed annularly about the needle and disposed distally of the needle notch, and a second O-ring disposed annularly about the needle and disposed proximally of the needle notch, the first O-ring and the second O-ring each extending between an outer surface of the needle and an inner surface of the needle channel to provide a fluid-tight seal therebetween. The needle is slidably engaged with the needle channel. In some embodiments, a portion of the blood flash channel is formed of a flexible tube. The catheter is a central venous catheter or a rapid insertion central catheter.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Figure 1A:
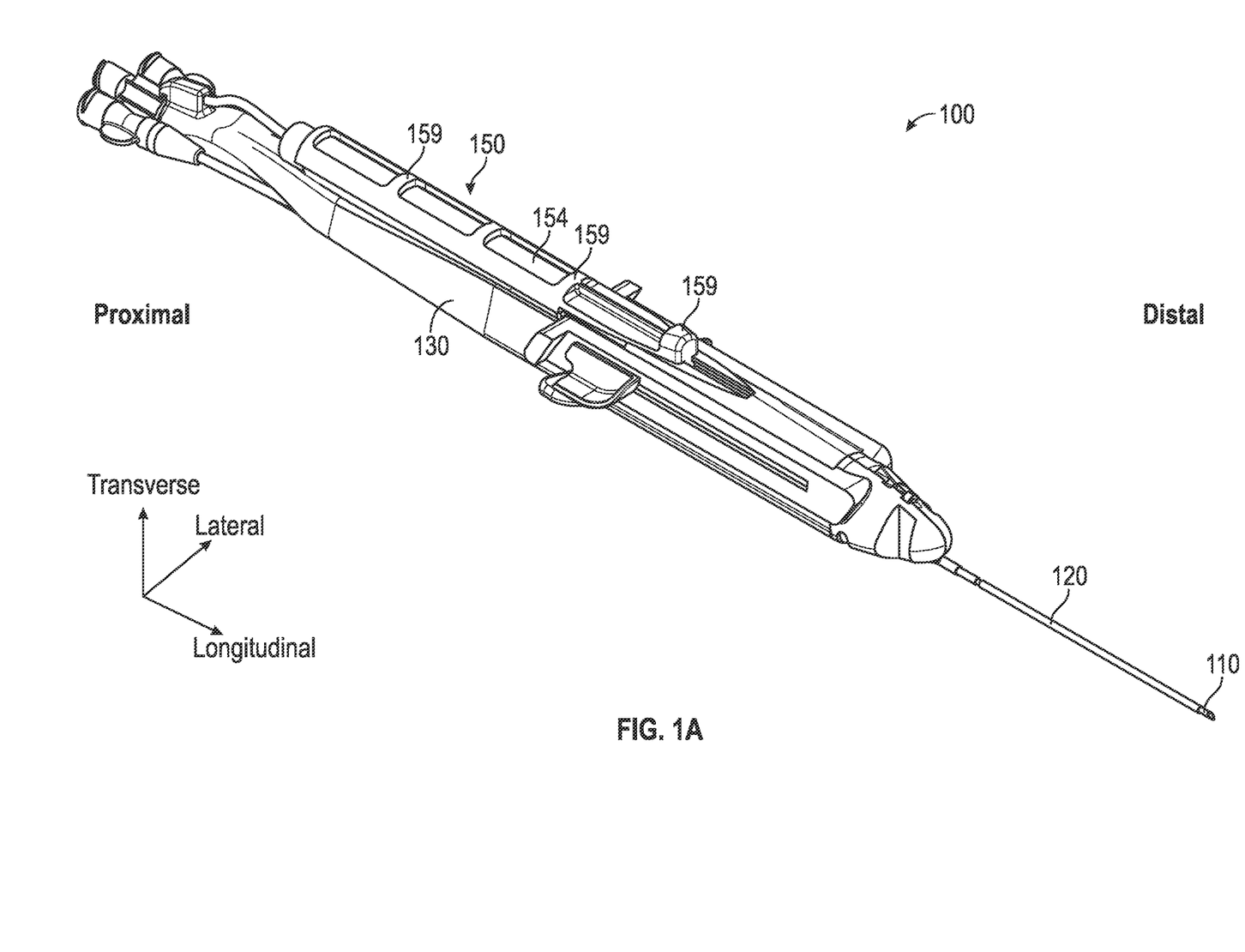
FIG. 1A shows a perspective view of an exemplary catheter insertion system, in accordance with embodiments disclosed herein.

To assist in the description of embodiments described herein, as shown in FIG. 1A, a longitudinal axis extends substantially parallel to an axial length of the catheter. A lateral axis extends normal to the longitudinal axis, and a transverse axis extends normal to both the longitudinal and lateral axes. Unless defined otherwise, all technical and scientific terms used herein have the same meaning as commonly understood by those of ordinary skill in the art.

Figure 1B:
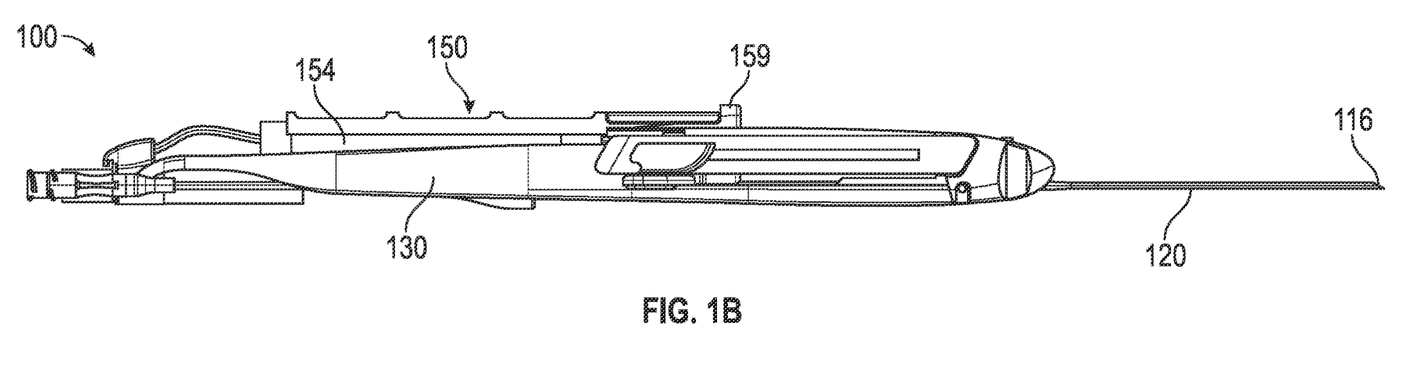
FIG. 1B shows a side view of an exemplary catheter insertion system, in accordance with embodiments disclosed herein.
Figure 1C:
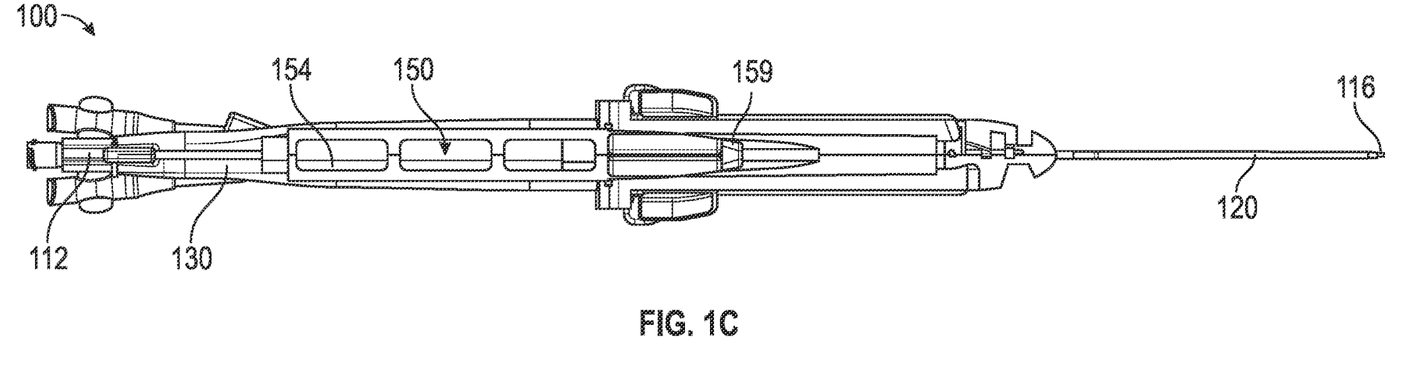
FIG. 1C shows a plan view of an exemplary catheter insertion system, in accordance with embodiments disclosed herein.
Figure 2:
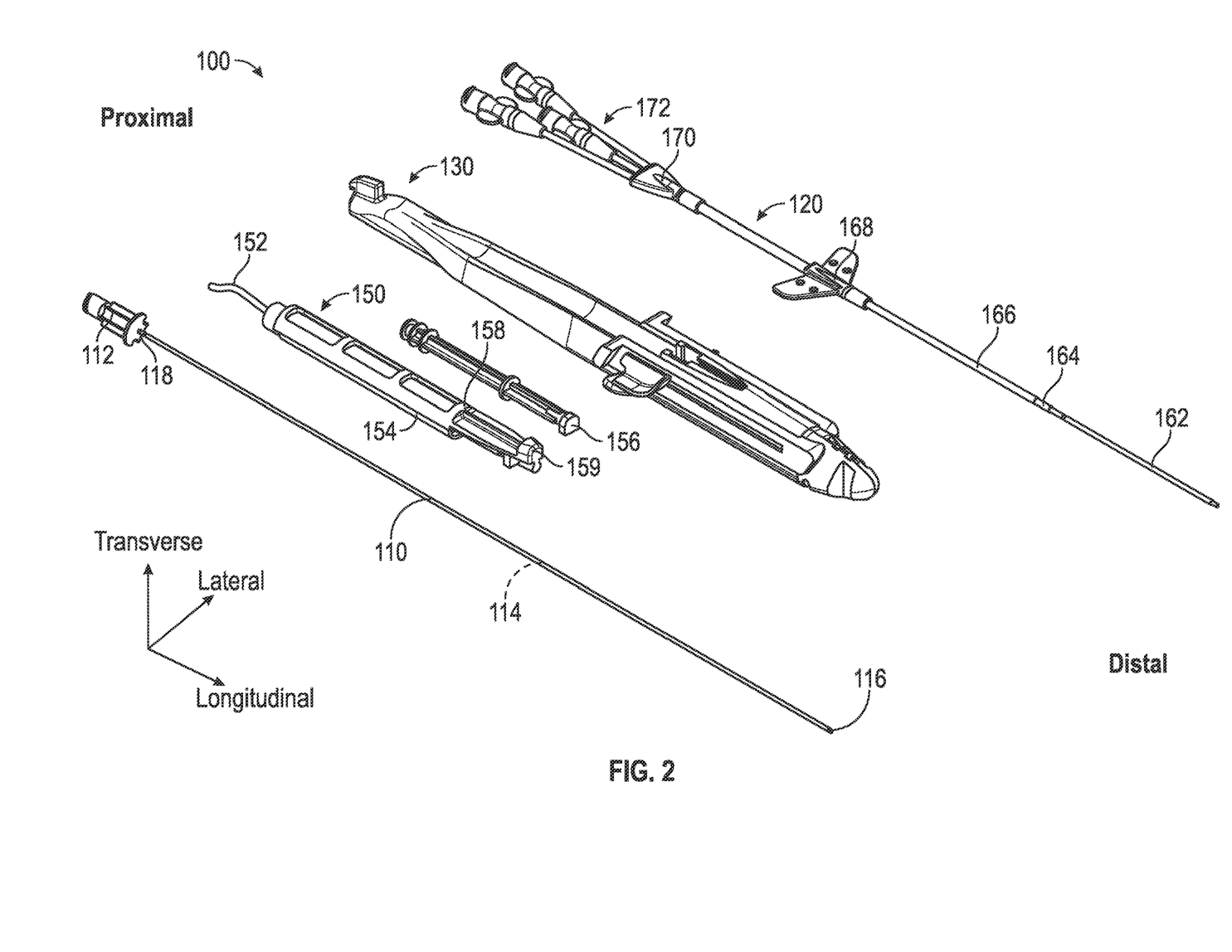
FIG. 2 shows an exploded view of an exemplary catheter insertion system, in accordance with embodiments disclosed herein.

FIGS. 1A-2 show an exemplary catheter insertion system ("system") 100, generally including a needle 110, a catheter 120, a housing 130, and a blood flash indicator 150. Optionally, the insertion system 100 can include one or more guidewires (not shown). The needle 110 can define a needle lumen 114 and can be supported by a needle hub 112 disposed at a proximal end thereof. The needle 110 can be configured to extend through at least a portion of a lumen of the catheter 120. A distal tip 116 of the needle 110 can extend distally of the distal tip of the catheter 120 and can define a sharpened tip configured for skin puncture and vascular access.

The catheter 120 can be a central venous catheter (CVC), a rapid insertion central catheter (RICC), or similar elongate catheter configured to provide access to a vasculature of a patient. As shown in FIG. 2, the catheter 120 can be a RICC catheter 120 including an access section 162 defining a first diameter, a dilation section 164, and a catheter body section 166 defining a second diameter, larger than the first diameter.

The access section 162 can define a single lumen and can be formed of a harder durometer material relative to the catheter body section 166. The catheter body section 166 can define one or more lumen and can be formed of a softer, more compliant material relative to the access section 162. The dilation section 164 can be formed of either the same material as the access section 162, or of a third material. The third material can be of a harder durometer relative to the material of the catheter body section 166. The dilation section 164 can provide a tapered transition between the first diameter of the access section 162 and the second diameter of the catheter body section 166. The access section 162 and the dilation section 164 can provide relatively more rigid mechanical properties and can be relatively more resistant to kinking or collapsing when an axial force is applied thereto, relative to the catheter body section 166. The catheter body section 166 can be relatively more compliant to facilitate negotiating tortuous vascular pathways. In an embodiment, the catheter 120 can further include a hub 168, a bifurcation 170, and/or one or more extension legs 172 each communicating with a lumen of the catheter 120. In an embodiment, the needle 110 can extend through an extension leg 172, through a lumen of the catheter body section 166 and through a lumen of the access section 162 to extend distally of a distal tip of the catheter 120.

In use, a clinician can access a vasculature using the RICC catheter 120 by insertion a needle tip 116 and a distal portion of the access section 162 into a vasculature. A blood flow can flow proximally through the needle lumen 114 to a blood flash indicator 150. A color and pulsatile flow can be observed to confirm correct vascular access. In case of incorrect vascular access, the access section 162 can be withdrawn and the insertion site closed by applying pressure, due to the relatively small diameter of the access section 162. Where correct vascular access is confirmed, the catheter 120 can be advanced, optionally over a guidewire, until a dilation section 164 enters the insertion site and dilates the insertion site to the second diameter of the catheter body section 166. The catheter body section 166 can then be advanced until a distal portion of the catheter 120 is at a target location within the vasculature. Further details of RICC catheters, associated insertion systems and associate methods thereof can be found in U.S. Pat. No. 10,376,675; U.S. Patent Publications U.S. 2019/0255294, U.S. 2021/0069471, U.S. 2021/0085927, U.S. 2021/0113809, U.S. 2021/0113810, U.S. 2021/0121661, U.S. 2021/0121667, U.S. 2021/0228843, U.S. 2021/0322729, U.S. 2021/0330941, U.S. 2021/0330942, and U.S. 2021/0361915, each of which are incorporated by reference in its entirety into this application.

As will be appreciated, depending on the configuration of the catheter insertion system, a blood flash flow would have to travel through the needle lumen 114, from a needle tip 116, substantially to a proximal end of the catheter 120 before exiting the catheter 120 and flowing distally to a blood flash indicator. Embodiments disclosed herein are directed to reducing the distance of travel between the needle tip 116 and the blood flash indicator 150.

In embodiments where the blood flash indicator is disposed towards the distal end of the device, the fluid path can be reduced by positioning the blood flash indicator 150 proximally. More specifically by placing the blood flash indicator 150 proximally of the catheter 120 center-of-mass, the length of the blood flash fluid path can reduced by between 20%-30%.

Figure 3A:
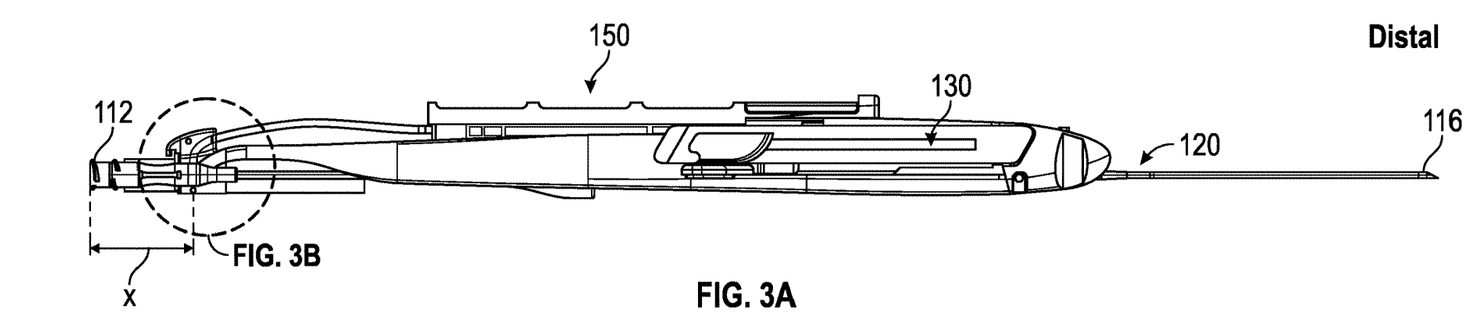
FIG. 3A shows a side, cut away view of an exemplary catheter insertion system, in accordance with embodiments disclosed herein.
Figure 3B:
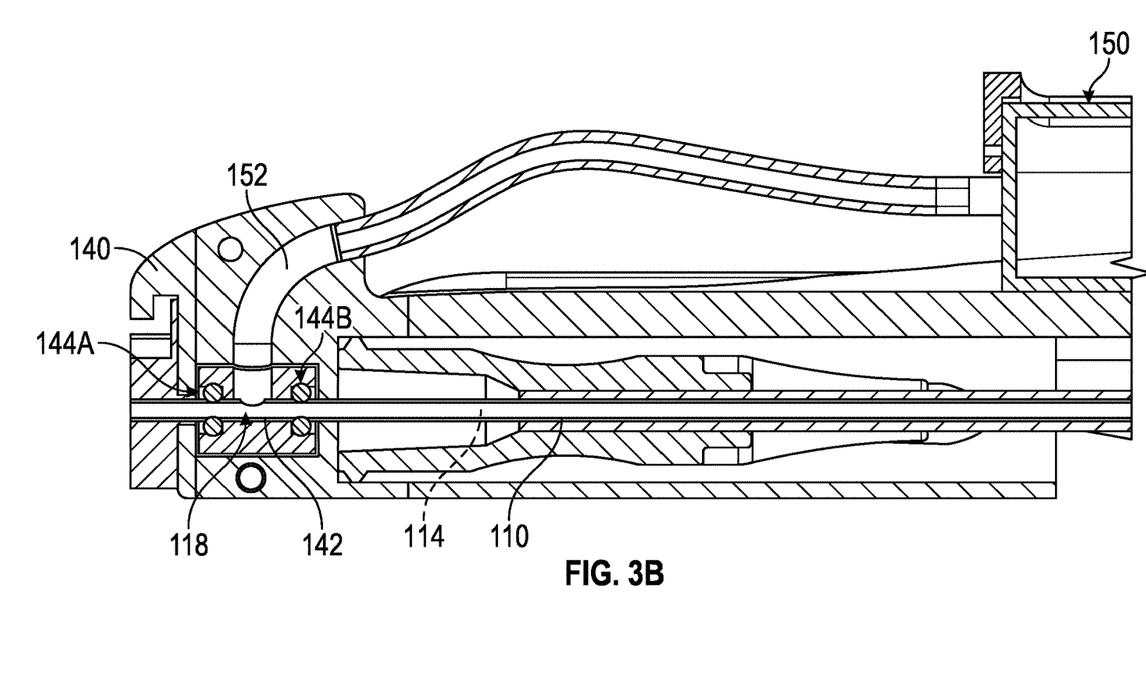
FIG. 3B shows a cross-section view of a needle interface of the catheter insertion system of FIG. 3A, in accordance with embodiments disclosed herein.

In an embodiment, as shown in FIGS. 3A-3B, the catheter insertion system 100 can include a needle interface 140 configured to provide fluid communication between the needle lumen 114 and the blood flash indicator 150, by way of a notch 118 disposed in a wall of the needle 110. The needle notch 118 can be positioned distally of the proximal end of the needle hub 112 by a distance (x). As such, the fluid path distance between the needle tip 116 and the blood flash indicator 150 can be further reduced by a distance (2x).

The needle interface 140 can define a needle channel 142 extending along a longitudinal axis and configured to receive a portion of the needle 110 therethrough. The needle 110 can be slidably engaged with the needle channel 142. The needle interface 140 can further include one or more O-rings 144 extending annularly about the needle 110 and disposed between an outer surface of the needle 110 and an inner surface of the channel 142, to provide a fluid tight seal therebetween.

The needle interface 140 can further include a blood flash channel 152 communicating between the needle channel 142 and the blood flash indicator 150. The blood flash channel 152 can extend substantially perpendicular from the needle channel 142 before extending towards the blood flash indicator 150. Prior to use, the needle notch 118 can be disposed within the needle channel 142, between a first O-ring 144A and a second O-ring 144B, and align with the blood flash channel 152. As the needle tip 116 is advanced into a vasculature, a blood flow can flow proximally through the needle lumen 114 through the notch 118 and into the blood flash channel 152 to the blood flash indicator 150. The first O-ring 144A and the second O-ring 144B can prevent a fluid flow from leaking between an outer surface of the needle 110 and an inner surface of the needle channel 142. The blood flow color or pulsatile flow can be observed to confirm correct vascular access. The needle 110 can then be withdrawn proximally through the needle channel 142 and, optionally, removed. In an embodiment, a portion of the needle 110 that is distal of the needle notch 118 can occlude the opening of the blood flash channel 152 with the needle channel 142 to seal the fluid therein.

In an embodiment, the blood flash indicator 150 can include a container configured to receive a blood flow therein. The container can be formed of a transparent material to allow a user to observe a color and pulsatile flow disposed therein. In an embodiment, the blood flash indicator 150 can include a vacutainer configured to maintain a vacuum therein to facilitate drawing a blood flow proximally through the needle lumen 114, through the needle notch 118, and into the vacutainer. In an embodiment, the vacuum can be maintained within the vacutainer by a portion of the needle 110 occluding the blood flash channel 152. When a user is ready to check for vascular access, the needle 110 can be advanced, relative to the housing 130, until the needle hub 112 abuts against the housing 130 and aligns the needle notch 118 with the blood flash channel 152. As such, the vacuum of the vacutainer is then placed in fluid communication with the needle lumen 114 and can facilitate drawing a blood flow proximally through the needle lumen 114.

In an embodiment, the blood flash indicator 150 can include a syringe barrel 154 and a plunger 156, slidably engaged therewith and configured to create a vacuum to draw a blood flow proximally through the needle lumen 114 and into the syringe barrel 154. In an embodiment, the operation of the syringe barrel 154 and plunger 156 can be reversed. For example, the plunger 156 can be fixedly engaged with the housing 130 to prevent any longitudinal movement relative thereto. The plunger 156 can be engaged with the housing 130 with an interference fit, snap-fit, press-fit engagement, adhesive, weld, bonding, or the like. The syringe barrel 154 can be supported by a barrel cradle 158. The barrel 154 and barrel cradle 158 assembly can be slidable relative to the plunger 156 and housing 130 assembly, and configured such that sliding the barrel 154 and cradle 158 assembly proximally can create a vacuum within the barrel 154. In an embodiment, the barrel cradle 158 can be formed of a transparent material to facilitate observing a blood flow therein.

Figure 4A:
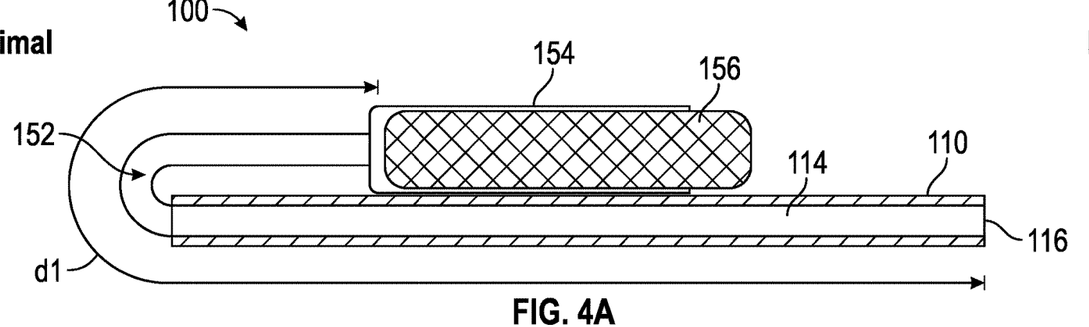
FIGS. 4A-4C show schematic views of a blood flash system for an exemplary catheter insertion system, in accordance with embodiments disclosed herein.
Figure 4B:
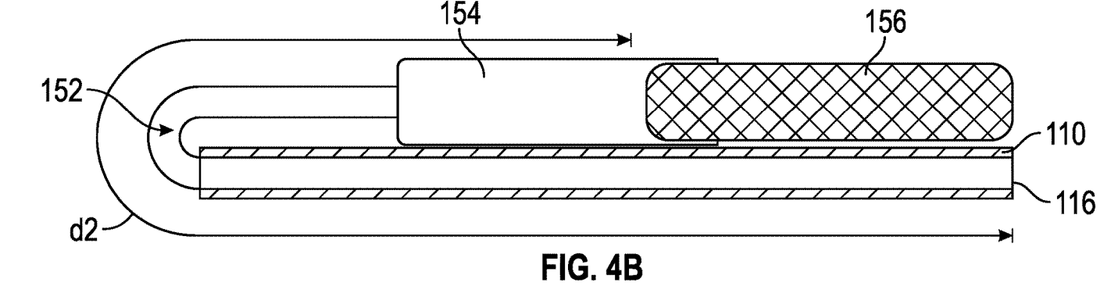
Figure 4C:
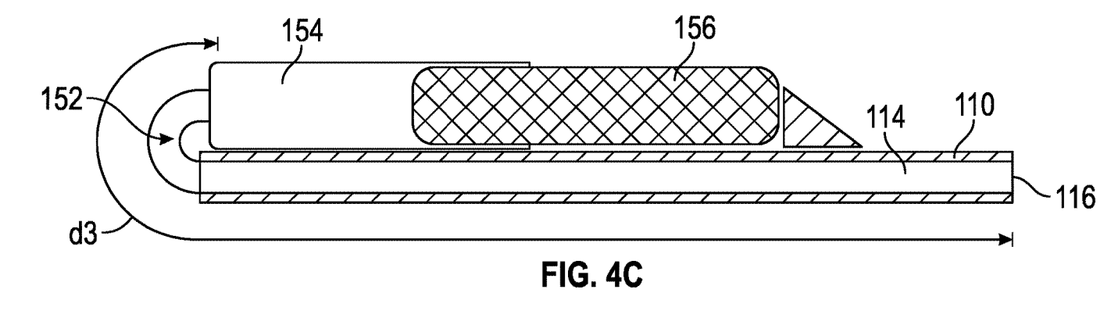

Advantageously, reversing the operation of the blood flash indicator syringe barrel 154 and plunger 156 can further reduce the fluid path between the needle tip and the blood flash indicator 150. For example, as shown in FIGS. 4A-4C, from a starting position shown in FIG. 4A, a blood flash fluid path can define a first distance (d1) extending from a needle tip 116 to a syringe barrel 154. As shown in FIG. 4B, where a blood flash indicator 150 includes a syringe barrel 154 and plunger 156 configured in a "conventional" way, the plunger 156 is withdrawn distally from the syringe barrel 154 to create the vacuum. However, in doing so the fluid path is extended from the first distance (d1) to a second distance (d2), which is greater than the first distance (d1).

By contrast, as shown in FIG. 4C, embodiments disclosed herein fix the plunger 156 to prevent any movement along a longitudinal axis, and the syringe barrel 154 slides proximally to create the vacuum. As such, a length of the fluid path is reduced from the first distance (d1) to a third distance (d3) that is less than the first distance (d1). By reversing the operation of the syringe blood flash indicator 150, the syringe barrel 154 can be slid proximally, towards the needle notch 118, to create the vacuum and thereby reducing a length of fluid path between the blood flash indicator 150 and the needle tip 116.

Advantageously, the action of the syringe barrel 154 and plunger 156 still allows a clinician to leverage the tactile and visual feedback offered via syringe-based blood flashback systems. Further, moving the syringe barrel 154 proximally moves the barrel 154 away from the distal end of the insertion device 100 providing a clearer line of sight at the insertion site and allows for additional operations to occur, for example the manipulation of guidewire advancement assemblies, catheter advancement assemblies, hinging housing portions, or the like.

In an embodiment, the barrel cradle 158 can include one or more gripping features 159 to facilitate grasping the syringe barrel 154 and urging the barrel 154 proximally. The gripping features 159 can include one or more abutments, finger loops, finger pad, ridges, ribs, or include materials having an increased friction co-efficient such rubber or silicone. In an embodiment, a portion of the blood flash channel 152, which provides fluid communication between the needle notch 118 and the syringe barrel 154, can include a flexible tube, or the like. Advantageously, the flexible tube can allow the syringe barrel 154 to slide proximally relative to the needle interface 140.

Figure 5:
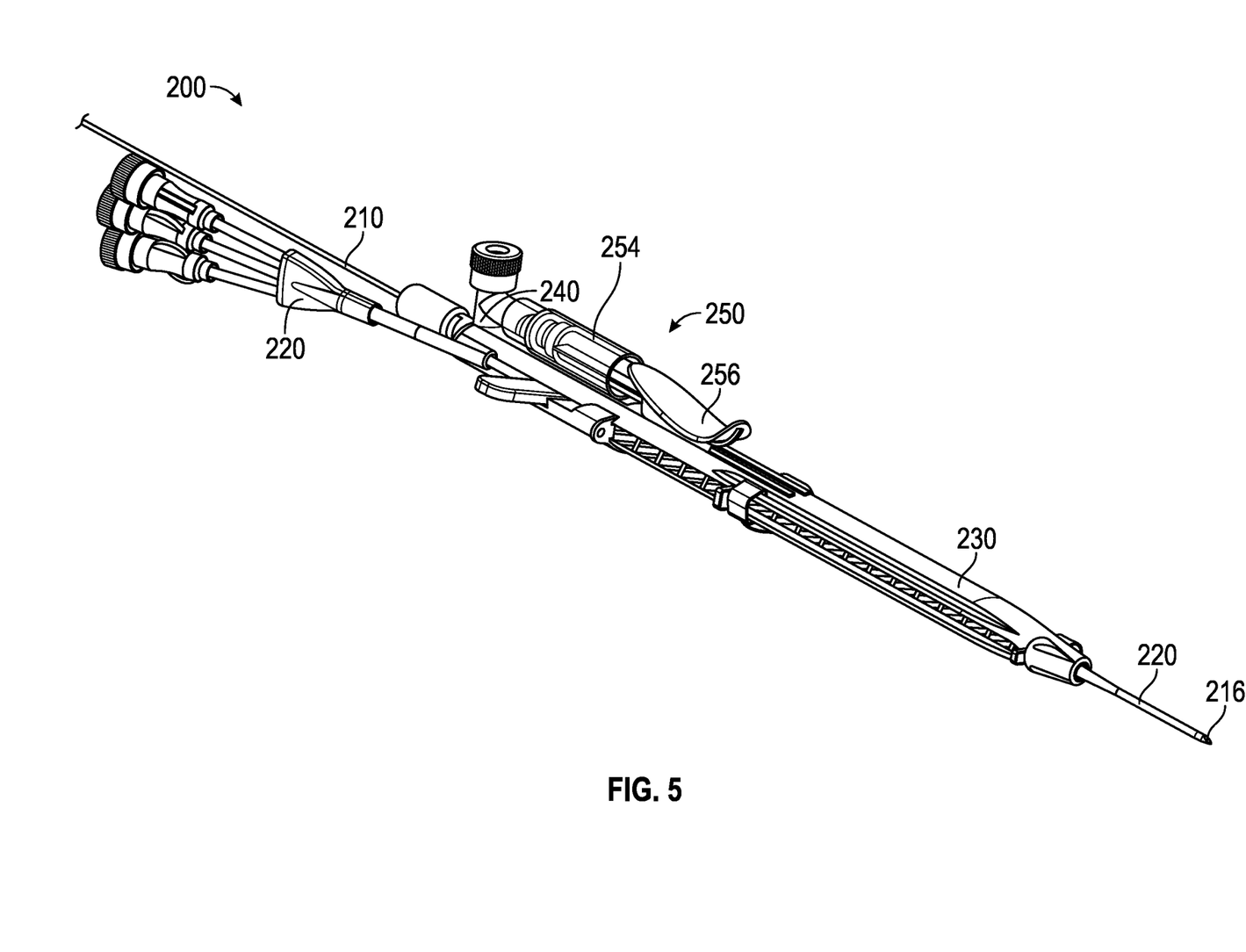
FIG. 5 shows a perspective view of an exemplary catheter insertion system, in accordance with embodiments disclosed herein.

In an embodiment, as shown in FIG. 5, an insertion system 200 can include a blood flash indicator system 250 that includes a syringe used in a "conventional" manner. The insertion system 200 can generally include a housing 230, a catheter 220 (e.g. a CVC catheter, or a RICC catheter), and a needle 210. Optionally the insertion system 200 can include one or more guidewires (not shown). The blood flash indicator system 250 can include a syringe barrel 254 coupled with a housing 230 to prevent relative longitudinal movement therebetween. A plunger 256 can be slidably engaged with the syringe barrel 254 and can be advanced distally to create a vacuum within the syringe barrel 254. As shown, the plunger 256 can include a finger pad to facilitate gripping of the plunger. A proximal end of the syringe barrel can be aligned adjacent with a needle notch (not shown) and needle interface 240, as described herein.

In use, the insertion system 200 can be advanced, until a needle tip 216 enters a vasculature of a patient. The plunger 256 can extend distally to allow a user to manipulate the plunger 256 while grasping a distal portion of the housing 230. Advancing the plunger 256 distally can create a vacuum within the syringe barrel 254 and draw a blood flow through the needle lumen to the needle notch, through a needle interface 240, through the blood flash channel and into the syringe barrel 254. As shown the syringe barrel 254 can be formed of a transparent material to facilitate observing a blood flow color and pulsatile flow. Advantageously, longitudinally aligning the proximal end of the syringe barrel 254 adjacent to the needle interface 240, the length of the blood flash channel can be reduced, further reducing the overall length of the blood flash fluid path.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A catheter insertion system, comprising:
   a catheter defining a catheter lumen and extending along a longitudinal axis;
   a needle defining a needle lumen and disposed within a portion of the catheter lumen;
   a housing supporting one of the catheter or the needle;
   a blood flash indicator including a plunger fixedly attached to the housing and a syringe barrel slidably engaged with the plunger along the longitudinal axis between a distal position and a proximal position; and
   a blood flash channel providing a fluid channel between the needle lumen and a proximal end of the syringe barrel, the blood flash channel providing a shorter fluid pathway when the syringe barrel is in the proximal position relative to the syringe barrel in the distal position.

2. The catheter insertion system according to claim 1, wherein the syringe barrel is configured to slide proximally relative to one of the plunger or the housing to create a vacuum and draw a blood flow through the needle lumen and into the syringe barrel.

3. The catheter insertion system according to claim 1, wherein the syringe barrel is formed of a transparent material to allow for observation of a blood color or pulsatile flow.

4. The catheter insertion system according to claim 1, wherein the syringe barrel is supported by a cradle including a gripping feature and configured to facilitate sliding of the syringe barrel along the longitudinal axis.

5. The catheter insertion system according to claim 1, wherein the housing includes a needle interface defining a needle channel, the needle channel configured to receive a portion of the needle extending therethrough and the blood flash channel providing fluid communication between the needle channel and the syringe barrel.

6. The catheter insertion system according to claim 5, wherein the needle includes a notch extending through a wall of the needle to provide fluid communication between the needle lumen and the needle channel.

7. The catheter insertion system according to claim 6, wherein the needle channel includes a first O-ring disposed annularly about the needle and disposed distally of the notch, and a second O-ring disposed annularly about the needle and disposed proximally of the notch, the first O-ring and the second O-ring each extending between an outer surface of the needle and an inner surface of the needle channel to provide a fluid-tight seal therebetween.

8. The catheter insertion system according to claim 5, wherein the needle is slidably engaged with the needle channel.

9. The catheter insertion system according to claim 5, wherein a portion of the blood flash channel is formed of a flexible tube.

10. The catheter insertion system according to claim 1, wherein the catheter is a central venous catheter or a rapid insertion central catheter.

* * * * *